United States Patent [19]

Mueller et al.

[11] Patent Number: 5,242,825
[45] Date of Patent: Sep. 7, 1993

[54] **BIOLOGICAL REMEDIATION OF CREOSOTE- AND SIMILARLY-CONTAMINATED SITES USING *PSEUDOMONAS PAUCIMOBILIS***

[75] Inventors: James G. Mueller; Peter J. Chapman, both of Gulf Breeze, Fla.

[73] Assignee: United States of America Environmental Protection Agency, Washington, D.C.

[21] Appl. No.: 913,274

[22] Filed: Jul. 14, 1992

Related U.S. Application Data

[62] Division of Ser. No. 371,241, Jun. 21, 1989, Pat. No. 5,132,224.

[51] Int. Cl.$^5$ .................... C12N 1/20; C07C 61/00; D06M 16/00; C02F 3/00
[52] U.S. Cl. .................... 435/253.3; 435/262.5; 435/264; 210/610
[58] Field of Search ................ 435/252.5, 264, 253.3; 210/610

[56] References Cited

U.S. PATENT DOCUMENTS

| | | | |
|---|---|---|---|
| 4,461,834 | 7/1984 | Mudder et al. | 435/253 |
| 4,468,461 | 8/1984 | Bopp | 435/253 |
| 4,477,570 | 10/1984 | Colaruotolo et al. | 435/253 |

*Primary Examiner*—Douglas W. Robinson
*Assistant Examiner*—Deborah K. Ware
*Attorney, Agent, or Firm*—Saliwanchik & Saliwanchik

[57] ABSTRACT

This invention concerns a biological process for remediating creosote-contaminated sites or environment sites containing polycyclic aromatic hydrocarbons generally found in creosote-contaminated sites. The biological process comprises novel bacterium, *Pseudomonas paucimobilis* strain EPA 505 sc., which can degrade recalcitrant chemical compounds.

1 Claim, 3 Drawing Sheets

BIOLOGICAL REMEDIATION OF CREOSOTE- AND SIMILARLY-CONTAMINATED SITES USING *PSEUDOMONAS PAUCIMOBILIS*

This is a division, of application Ser. No. 07/371,241, filed Jun. 21, 1989 just now patented, U.S. Pat. No. 5,132,224.

BACKGROUND OF THE INVENTION

In 1980, the U.S. Environmental Protection Agency concluded that waste water from creosote and PCP wood-preserving processes poses an immediate or potential hazard to human health and the environment when improperly treated, stored, or disposed of. Moreover, pond sediments and sludges contaminated with wood preservatives were considered hazardous. Such materials are categorized as K001 hazardous wastes (49 CFR ch.1 subpart 172.101).

Creosote contamination is generally associated with surface soils, waters in treatment lagoons or evaporation areas, and groundwater contaminated with leachate from the above sources. There are approximately 550 sources of such waste in the United States where wood preserving is currently conducted (Micklewright, J. T. [1986] *Contract report to the American Wood-Preserver's Institute*. International Statistics Council, Inc., Washington, D.C.). Collectively, active treatment facilities generate an estimated 840 to 1530 dry metric tons of K001 sludge annually (Sikora, L. J. [1983] In *Land Treatment of Hazardous Wastes*, Parr, J. G., P. B. Marsh, eds.; Noyes Data Corp., Park Ridge, N.J., pp. 397–410). Although the number of operating wood-preserving facilities has been reduced, it has been estimated that there are 700 sites throughout the United States where wood preservation is, or has been, conducted (Burton, M. B., M. M. Martinson, K. D. Barr [1988] *Biotech USA*. 5th Ann. Indust. Conf., Nov. 14–16, San Francisco, CA). Since creosote treatment sites are commonly impacted by leaking tanks, drippings from treated lumber, spills, and leachate from unlined holding ponds, this number presumably describes the number of creosote-contaminated sites as well.

A major concern when discussing creosote contamination focuses on persistence of toxic constituents. Under appropriate conditions, all creosote constituents are potentially degradable. Therefore, persistence tends to be a function of impregnation within the wood as opposed to an inherent recalcitrance. For example, Petrowicz and Becker (Petrowicz, H. J. and G. Beckare [1964] Materialprufung 6:461–570) demonstrated that creosote constituents were recovered from creosote-treated wooden blocks; 16 of these compounds were identified as naphthalene, 2-methylnaphthalene, biphenyl, dimethylnaphthalene, acenaphthene, dibenzofuran, fluorene, methylfluorene, (anthracene and phenanthrene), carbazole, methylphenanthrene, 2-phenylnaphthalene, fluoranthene, pyrene, 2,3-benzo[b]fluorene, and chrysene. The same chemicals were recovered from unweathered blocks.

Becker and Petrowicz (Becker, G. and H. J. Petrowicz [1965] Materialprufung 7:325–330) showed that more than 30 years after initial application, creosote-treated railroad ties exhibited only a minor change in creosote composition. Rotard and Mailahn (Rotard, W. and W. Mailahn [1987] Anal. Chem. 59:65–69) employed more refined analytical techniques and found a significant amount of creosote present in discarded railroad crossties that had been installed in playgrounds. The most common constituents identified were (in order of decreasing concentration) phenanthrene, anthracene, fluoranthene, pyrene, chrysene, benzo[a]pyrene, benzo[b]fluoranthene, and benzo[j]fluoranthene.

Coal-tar creosote has been widely used as a wood preservative for over 150 years with an anual consumption in 1986 estimated at 454,000 metric tons (Mattraw, H. C. Jr., and B. J. Franks [1986] Chapter A. "Description of hazardous waste research at a creosote works, Pensacola, FL," pp. 1–8. In A. C. Mattraw, Jr., and B. J. Franks [eds.], USGS survey of toxic wastes-groundwater contamination program. USGS Water Supply Paper No. 2285). Though creosote-treated products themselves do not appear to represent a threat to the environment, accidental spillage and improper disposal of creosote at production plants and at wood-preserving facilities have resulted in extensive contamination of soil, surface water, and groundwater aquifers (Fisher, C. W., and G. R. Tallon [1971] Proceed. Am. Wood-Preservers' Assoc. 67:92–96; Goerlitz, D. F., D. E. Troutman, E. M. Godsy, and B. J. Franks [1986] Chapter G, pp. 49–53. USGS Water Supply Paper No. 2285). Since creosote contains many toxic compounds and priority pollutants, such sites are considered hazardous; hence, remedial action is required.

Recent studies have suggested that biodegradation may represent a clean and efficient means of remediating such sites. It has also been reported that 85% of creosote consists of polycyclic hydrocarbons (PAH's). Therefore, biodegradation of these constituents would result in the removal of a significant volume of creosote pollutants. Moreover, the destruction of these components would significantly reduce the potential health hazards associated wtih creosote-contaminated environments. Likewise, other environments similarly affected by PAH's (i.e., oil refineries, coal gasification sites) may also be improved significantly by removing the hazards associated with this class of chemical pollutant.

Microorganisms capable of degrading certain creosote PAH's have been described, and mechanisms for PAH biodegradation have been reviewed (Cerniglia, C. E., and S. K. Yang [1984] Appl. Environ. Microbiol. 47:119–124). Microbial degradation of lower molecular weight PAH's such as naphthalene and biphenyl by a variety of bacterial strains is well established. Biodegradation of tricyclic compounds such as anthracene and phenanthrene has also been reported.

There appear to be no accounts of the microbial utilization of PAH's containing four or more aromatic rings. However, several publications have described the co-metabolism of such PAH's including benzo[a]anthracene, benzo[a]pyrene, fluoranthene, and pyrene. Incidental metabolism of various PAH's by the ligninolytic fungus *Phanerochaete chrysosporium* grown under defined conditions has also been reported.

The basic principle of bioremediation is to exploit the ability of microorganisms to catabolize a wide range of organic substrates. Trickling filtration, land-farming, activated sludge, oxidation lagoons, and soil inoculation represent a few means in which microorganisms are utilized to treat industrial wastes in situ. For bioreactor operations, engineering designs are based on the unique demands of a particular microbial consortium or pure culture so as to provide the ideal environment, thereby optimizing the process. When successful, bioremediation results in the conversion of a toxic chemical to non-toxic materials.

Though there has been a large amount of research concerning the remediation of creosote-contaminated sites, there remains a need for more effective biological systems to accomplish this goal. The invention, described and claimed herein, is directed to the use of novel microbes which can be used to remediate creosote-contaminated sites.

BRIEF SUMMARY OF THE INVENTION

The subject invention relates to the use of novel microbes to remediate creosote- or similarly-contaminated sites. Specifically exemplified is the use of a novel 7-membered bacterial consortium to remediate creosote-contaminated sites. This 7-membered bacterial consortium was isolated from a sandy soil highly contaminated with coal-tar creosote. Though isolation was accomplished by the use of an enrichment culture employing serial transfer through a mineral salts medium containing fluoranthene, other recalcitrant chemical compounds, for example, as disclosed herein, can be used.

The ability of this consortium to degrade fluoranthene and other polycyclic aromatic hydrocarbons (PAH's) was verified by demonstrating their disappearance from an artificial PAH mixture using capillary gas chromatography. When grown on fluoranthene as sole carbon source and subsequently exposed to fluoranthene plus 16 additional PAH's typical of those found in creosote, this consortium exhibited the capacity to remove all PAH's present in this defined mixture. After 3 days of incubation, 13 of the original 17 PAH components were degraded to levels below the limit of detection (10 ng/L). Continued incubation resulted in extensive degradation of the remaining 4 compounds. Since this consortium is able to utilize a high molecular weight PAH as sole carbon source, in conjunction with its ability to transform a diverse array of PAH's, it can be used to remediate environments contaminated with PAH's such as those impacted by creosote.

We have isolated a particularly effective PAH-degrading microbe from this 7-membered consortium. This novel microbe has been designated *Pseudomonas paucimobilis* strain EPA505sc.

The microbes of the subject invention can be used in various known procedures for cleaning up creosote- or similarly-contaminated sites. For example, procedures such as soil percolation, activated sludge, and bioreactors can be used alone or in combination.

DETAILED DISCLOSURE OF THE INVENTION

Figure 1A:
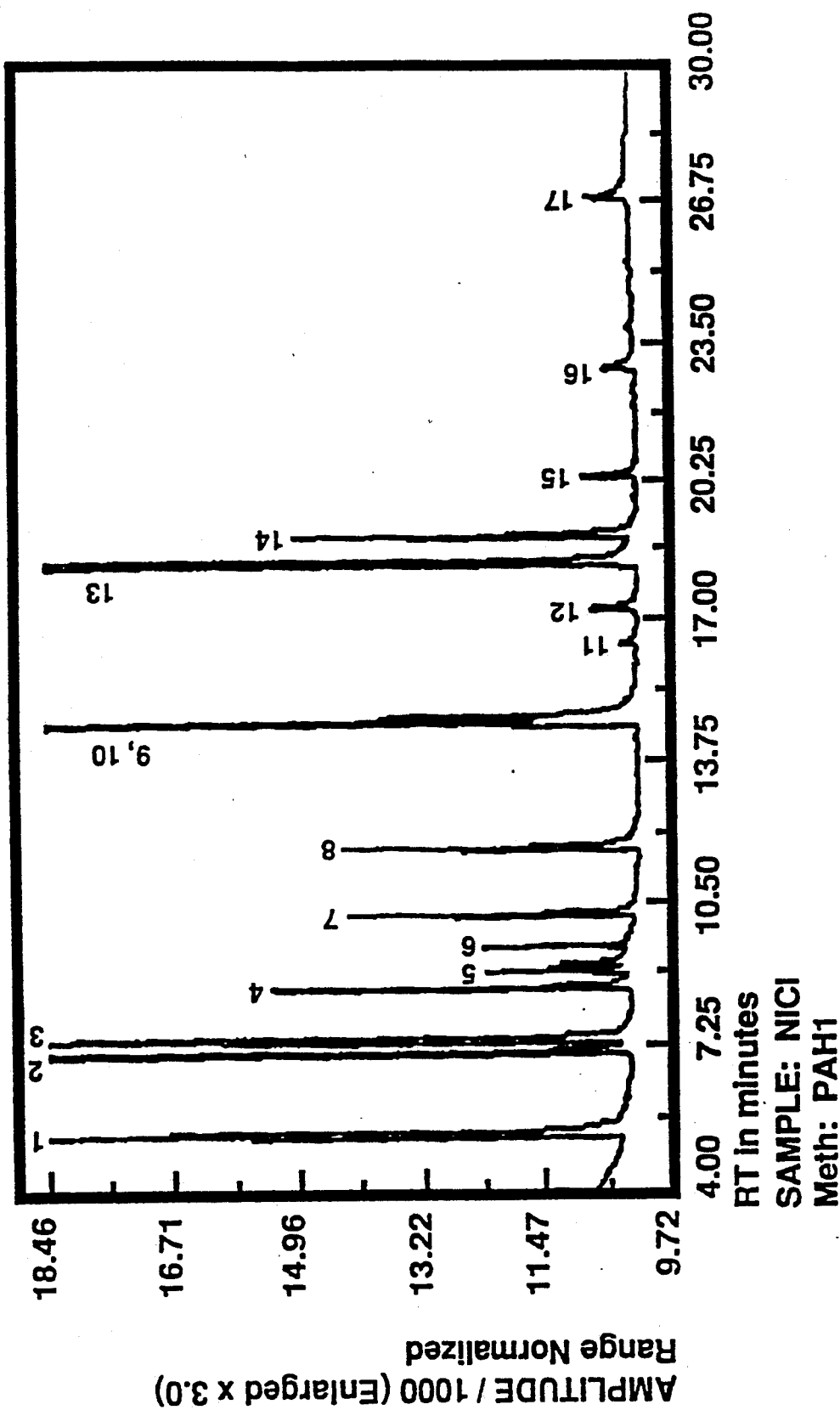
FIG. 1 presents gas chromatograms of methylene chloride extracts of MS+PAH broths either uninoculated (FIG. 1a), inoculated with *Pseudomonas putida* [NAH7] strain PpG7 (ATCC 17485) (FIG. 1b), or inoculated with the fluoranthene-induced consortium (FIG. 1c). With the exception of two formalin-associated peaks at 3.6 and 6.5 min, the gas chromatograms of the killed-cell controls were essentially identical to that presented in FIG. 1a. After 8 days incubation, there were no detectable losses of PAH's from the uninoculated controls. In the presence of PpG7, only naphthalene (peak 1) and 2-MN (peak 2) were degraded beyond the limit of detection. The fluoranthene-induced consortium, however, exhibited extensive degradation of all the PAH's present in the defined mixture. Only fluoranthene (peak 13) and pyrene (peak 14) were present in detectable amounts (Table 3). Though the fluoranthene peak does not appear to have been significantly reduced, the area associated with this peak corresponds to 41.6% recovery which, in turn, corresponds to degradation of 0.25 mg fluoranthene in 8 days.
Figure 1B:
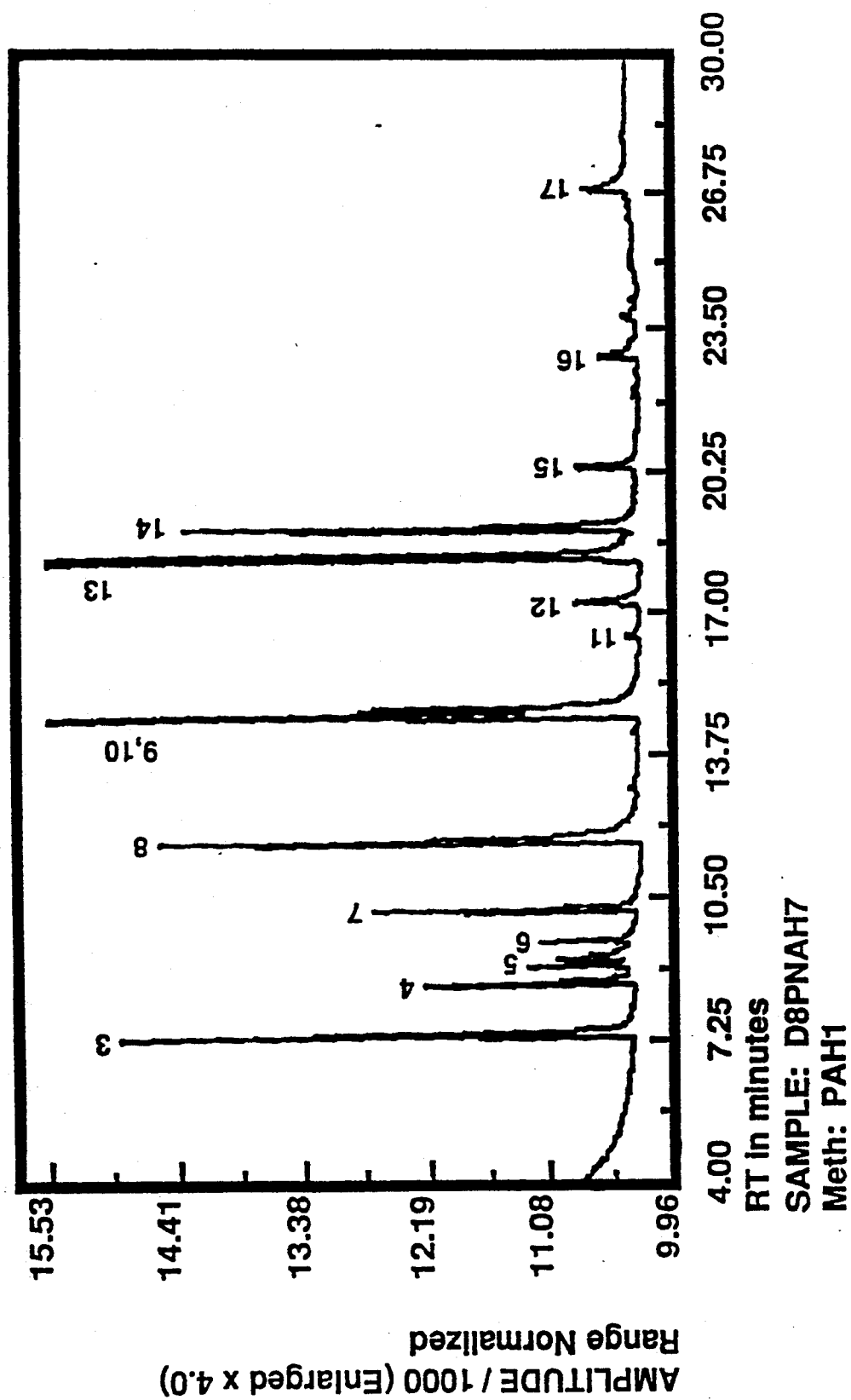
Figure 1C:
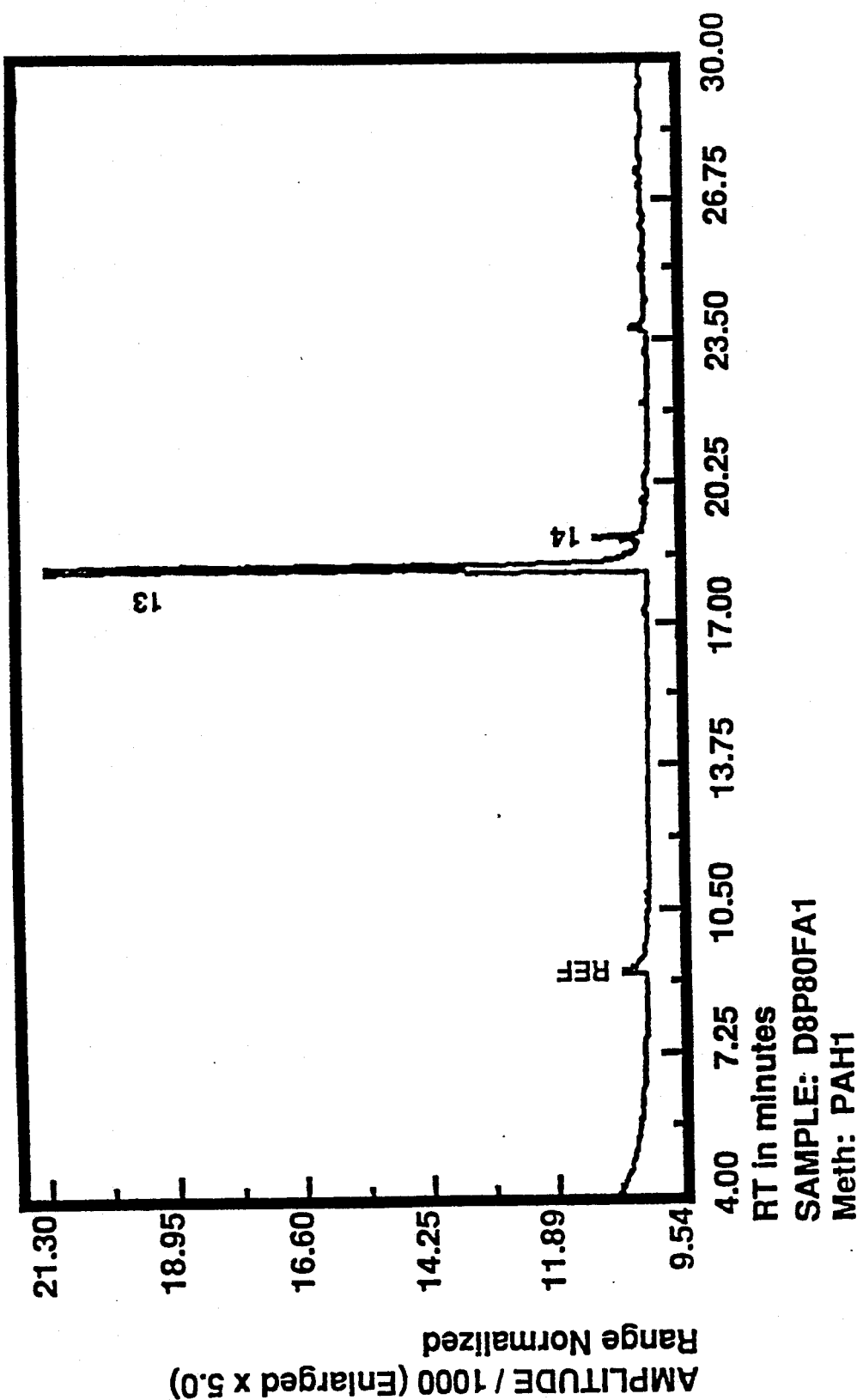

Creosote- or similarly-contaminated sites can be remediated by use of the 7-membered bacterial consortium of the invention. Particularly useful is the isolate designated *Pseudomonas paucimobilis* strain EPA505sc.

A subculture of has been deposited in the permanent collection of the Northern Research Laboratory, U.S. Department of Agriculture, Peoria, Ill., USA on Jun. 9, 1989. The accession number is as follows:

*Pseudomonas paucimobilis* strain EPA505sc-NRRL B-18512

The taxonomy of *Pseudomonas paucimobilis* strain EPA505sc is as follows: Gram-negative, aerobic, non-glucose fermenting, motile (weakly) rod ($0.5 \times 1.5$ $\mu$m). Forms a 1.0 to 2.0 mm bright yellow colony on nutrient agar plus 0.5% glucose after 5 days at 28° C. Yellow pigment is non-diffusible and non-fluorescent. Oxidizes glucose, D-gluconate, and lactose. Hydrolyses esculin. Does not assimilate arabinose, maltose, mannose, malate, N-acetyl-D-glucosamine, caprate, adipate, TWEEN TM 80, citrate, or phenylacetate. Does not reduce nitrate of nitrite. Negative reactions for urease, arginine dihydrolase, gelatinase, and tryptophanase.

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The novel microbes of the invention can be used, advantageously, in combination with a solubilizing agent. Examples of solubilizing agents which can be used in the subject invention are the many well-known and commercially available non-ionic and anionic surface active agents and detergents. Some examples are TWEEN TM 80 (a non-ionic surfactant available from Fisher Chemical Co.), Merpol (a non-ionic ethylene oxide condensate produced by E. I. duPont de Nemours and Co., Inc.), Consowet (a dioctylsulfosuccinate anionic detergent produced by Consos, Inc., Charlotte, N.C.), and Astrowet (a dioctylsulfosuccinate anionic detergent produced by Astro American Chemical Co., Greenville, S.C.). Generally, the basic chemical structure or nature of these solubilizing agents is not limiting so long as they can be considered to be nonionic or anionic surface active agents or detergents.

The creosote-or similarly-contaminiated site degradation procedure itself, using the novel microbes isolated by the process of the subject invention, can be carried out by use of various known procedures. For example, the degradation process can be carried out by adding liquid culture media of a novel microbe to contaminated soil or water wastes. Generally, procedures as disclosed in U.S. Pat. Nos. 4,477,570 and 4,483,923 can be used. As any person skilled in this art knows, good growth conditions for the degrading microbes must be employed in order to enable the microbes to degrade contaminated sites effectively. Determination of such optimum growth conditions are routine for the skilled artisan.

Following are examples which illustrate procedures, including the best mode, for practicing the invention. These examples should not be construed as limiting. All percentages are by weight and all solvent mixture proportions are by volume unless otherwise noted.

EXAMPLE 1

Source of Creosote-Degrading Microorganisms

Soil highly contaminated with coal-tar creosote was freshly obtained from a nearby creosote-waste site in Pensacola, Fla. At one location at this site a former evaporation pond for creosote-contaminated waste water resulted in the formation of a 2-inch layer or tar-like sludge heavily contaminated with more than 50% (weight) methylene chloride-extractable organics. This layer was located approximately 6 inches below the soil surface. Soil immediately adjacent to this sludge was collected from depths of 4 to 8 inches and was used as the source of microorganisms. Detailed reports on the history of creosote use, type and amount of pollutants present, and the extent of environmental contamination at this site are available (Godsy, E. M., and D. F. Goerlitz [1986] In A. C. Mattraw, Jr., and B. J. Franks [eds.], USGS survey of toxic wastes—groundwater contamination program. USGS Water Supply Paper No. 2285, Chapter H, pp. 55–58; Pereira, W. E., and C. E. Rostad [1986] USGS Water Supply Paper No. 2285, Chapter E, pp. 33–40; Troutman, D. E., E. M. Godsy, D. F. Goerlitz, and G. G. Ehrlich [1984] "Phenolic contamination in the sand and gravel aquifer from a surface impoundment of wood treatment wastes, Pensacola, Fla., " USGS Water Resources Invest. Report No. 84–4231, 36p.)

EXAMPLE 2

Mineral Salts + PAH Medium

The mineral salts (MS) medium used consisted of (mg/L): $(NH_4)_2SO_4 = 1000$; $KH_2PO_4 = 200$; $MgSO_4.7H_2O = 200$; $CaCl_2.2H_2O = 100$; $FeCl_3.6H_2O = 5$; $(NH_4)_6Mo_4O_{24}.4H_2O = 1$. To achieve the aqueous PAH concentrations reported in Table 1, TWEEN ™ 80 (Fisher Chemical Co.) was added at 200 mg/L. The pH was adjusted to pH=7.0 with 0.1N HCl and the medium was sterilized (104 kPa, 121° C., 20 min.) prior to the addition of organic substrates. Polycyclic aromatic hydrocarbons (Sigma Chemical Company) used were of the highest purity (>98%) available).

To prepare an aqueous solution containing a defined mixture of PAH's closely related to the PAH composition of creosote, the appropriate amount of each compound (Table 1) was added to a sterile flask and dissolved in 5.0 ml methylene chloride to effect sterilization. Methylene chloride was removed under a stream of dry nitrogen passed through a 0.25 μm filter and the PAH's were dissolved by mixing with a magnetic stir bar into an appropriate amount of sterile MS medium. After mixing for 6 hours at room temperature, the medium designated MS+PAH was filtered through a layer of sterile glass wool to remove undissolved solids. Medium was stored at 1° C. in sterile, 1.0 L Wheaton bottles fitted with Teflon-lined screw-caps. The concentration of each compound was determined by capillary gas chromatography of extracted samples as described in following sections.

TABLE 1

Composition of a defined polycyclic aromatic hydrocarbon (PAH) mixture and its relationship to predominant PAH's found in coal-tar creosote.

| Peak number[1] | compound | abbreviation (if used) | Aqueous solubility[2] (25° C.) mg/L | defined PAH mixture[3] mg/L | coal tar creosote[4] range % - total PAH |
|---|---|---|---|---|---|
| 1 | naphthalene | — | 31.7 | 17.1 | 3.0–15.8 |
| 2 | 2-methylnaphthalene | 2-MN | 25.4 | 17.1 | 2.1–14.2 |
| 3 | 1-methylnaphthalene | 1-MN | 28.5 | 16.0 | 2.1–14.2 |
| 4 | biphenyl | — | 7.5 | 5.8 | 2.3–2.8 |
| 5 | 2,6-dimethylnaphthalene | 2,6-DMN | 2.0 | 2.1 | 2.0–2.3 |
| 6 | 2,3-dimethylnaphthalene | 2,3-DMN | 3.0 | 1.9 | 2.0–2.4 |
| 7 | acenaphthene | — | 3.9 | 3.8 | 4.1–9.0 |
| 8 | fluorene | — | 2.0 | 3.9 | 8.6–10.0 |
| 9 | phenanthrene | — | 1.3 | 7.0 | 4.6–21.0 |
| 10 | anthracene | — | 0.07 | 2.7 | 1.5–2.0 |
| 11 | 2-methylanthracene | 2-MA | 0.04 | 0.2 | 0.5–2.6 |
| 12 | anthraquinone | — | — | 0.9 | 0.1–1.0 |
| 13 | fluoranthene | — | 0.26 | 8.7 | 6.8–10.4 |
| 14 | pyrene | — | 0.14 | 2.3 | 2.2–8.5 |
| 15 | 2,3-benzo[b]fluorene | 2,3-BBF | 0.002 | 0.4 | 2.0–4.6 |
| 16 | chrysene | — | 0.002 | 0.3 | 2.8–3.0 |
| 17 | benzo[a]pyrene | BAP | 0.003 | 1.2 | 0.1–1.0 |

TABLE 1-continued

Composition of a defined polycyclic aromatic hydrocarbon (PAH) mixture
and its relationship to predominant PAH's found in coal-tar creosote.

| | | | PAH concentration in | |
|---|---|---|---|---|
| Peak number[1] | compound | abbreviation (if used) | Aqueous solubility[2] (25° C.) mg/L | defined PAH mixture[3] mg/L | coal tar creosote[4] range % - total PAH |
| | TOTAL: | | | 91.4 | |

[1]order of elution through capillary column SBP-5 (Supelco)
[2]Baker, R. J., W. E. Acree, Jr., and C. C. Tsai (1984) Quant. Struct.-Act. Relat. 3:10-16; Mackay, D., and W. Y. Shiu (1977) J. Chem. Eng. Data 22:399-402.
[3]Increased solubility in the presence of 200 mg/L TWEEN ™ 80
[4]Ranges based on analyses by Andersson, K., J. O. Levin, and C. A. Nilsson (1983) Chemosphere 12:197-207; Becker, G. (1977) Proceed. Am. Wood-Preservers' Assoc. 73:16-25; Borowitzky, H., and G. Schomburg (1979) J. Chrom. 170:99-124; Lorenz, L. J., and L. R. Gjovik (1972) Proceed. Am. Wood-Preservers' Assoc. 68:32-41; Nestler, F. H. M. (1974) Fuel 60:213-220; Novotny, M., J. W. Strand, S. L. Smith, D. Wiesler, and F. J. Schwende (1981) Fuel 60:213-220.

EXAMPLE 3

Fluoranthene (A Recalcitrant Chemical) Enrichment Cultures

A MS+fluoranthene medium was prepared according to the protocol in Example 1, with the following modifications: (1) an excess of fluoranthene (approximately 500 mg/L) was supplemented for the other organic components shown in Table 1; (2) suspended solids were not removed; and (3) TWEEN ™ 80 was not added. Fifty ml of this medium were transferred to a 250 ml screw-cap Erlenmeyer flask and inoculated with 1.0 g (wet weight) creosote-contaminated soil passed through a 50-mesh sieve. Flasks were incubated in the dark (28±1° C., 175 cycles/min) under controlled conditions. After 5 days incubation, a 5.0 ml aliquot was diluted 1:10 (vol/vol) with fresh MS+fluoranthene broth and incubated for 3 days. Subsequent samples were diluted 1:50 with the same medium every 3 days. Following several such transfers, disappearance of undissolved fluoranthene crystals was visually apparent. Fluoranthene-utilizers were maintained by regularly diluting established cultures 1:50 with fresh MS+fluoranthene broth every 14 days.

EXAMPLE 4

Partial Characterization of Fluoranthene-Utilizing Microbe Consortium

Numerous aliquots from fluoranthene-enrichment cultures of various ages were streaked for isolation on Nutrient Agar (Difco, Detroit, Mich.) amended with 0.5% glucose (NAG agar). After 5-14 days incubation at 28° C., colonies representative of each of the different morphological types were removed and the single colonies repeatedly purified on NAG agar. Ultimately, 7 morphologically distinct, Gram-negative bacteria were isolated in pure culture. These organisms were designated EPA50FAE 1, 2, 3, 4, 5, 5b, and 6.

To ensure that all organisms essential for fluoranthene-utilization had been isolated, MS+fluoranthene broth was inoculated with all seven isolates to reconstitute the consortium, and fluoranthene degradation was assessed. The consortium was reconstituted by removing single colonies is each organism from NAG plates and suspending them in sterile MS medium to uniform density (%T$_{600}$=50±2.0). Fifty ml of MS+fluoranthene broth were inoculated with 0.2 ml of each suspension and incubated at 28° C. with aeration (175 cycles/min). Fluoranthene utilization was qualitatively assessed by recording visually apparent increases in microbial biomass, spectral (color) changes, and disappearance of fluoranthene crystals. The sequence of color changes in the medium was from colorless to bright orange to bright yellow to a light brown which was maintained after fluoranthene crystals were no longer visible. Exhausted cultures to which additional fluoranthene was added completed this sequence in two days. Qualitative increases in microbial biomass were evident. However, since the fluoranthene cultures exhibited a strong tendency to form rapidly settling clumps, increases in microbial biomass could not be measured quantitatively.

When plated on a complex medium such as NAG agar (Nutrient Agar, Difco, amended with 0.5% glucose), a total of seven morphologically distinct, Gram-negative bacteria were isolated. This 7-membered consortium maintained its integrity throughout the enrichment procedure and through repeated serial transfers, thereby reflecting stability. When MS+fluoranthene broth was inoculated with the reconstituted consortium, fluoranthene degradation was again obvious. However, there was an initial lag of 5 to 7 days before fluoranthene degradation became apparent. After this period, fluoranthene degradation was rapid (<2 days).

Table 2 summarizes percent recovery from MS+PAH broths of 17 PAH's present in the defined mixture 3 days after inoculation with either the fluoranthene-induced consortium or with *P. putida* PpG7. Extraction efficiencies and losses attributable to abiotic processes were accounted for by comparing recovery values for each compound with that obtained from the killed cell controls. With the exception of naphthalene (84.3%) and 2,3-DMN (78.9%), percent recovery from abiotic controls was greater than 85%.

The ability to detect selective utilization of individual components of the defined mixture was demonstrated with the culture inoculated with PpG7. After 3 days incubation, only naphthalene and 2-MN were extensively degraded. These data were identical to those obtained after 5, 8, and 14 days incubation (data not shown).

When the consortium was grown on fluoranthene and subsequently exposed to fluoranthene plus 16 other PAH's, the fluoranthene-induced consortium exhibited the ability to degrade all of the PAH's present in the defined mixture (Table 2). After 3 days incubation, 13 of the original 17 PAH's were degraded below the limits of detection (10 ng/L). Additionally, greater than 90% degradation of anthracene and anthraquinone was evidenced by their percent recoveries, 1.5 (±1.5) and 6.5 (±6.5), respectively. The remaining 2 compounds, fluoranthene and pyrene, were also degraded as demonstrated by respective recoveries of 69.5 (±13.6) and 44.3 (±8.5).

TABLE 2

Biodegradation of 17 PAH's by a 7-membered, fluoranthene-induced bacterial consortium isolated from a creosote waste site.

| | % recovery of select PAH's from broth culture after 3 day incubation with | | |
|---|---|---|---|
| Compound[1] | Fluoranthene-induced consortium | Killed cell control[2] | P. putida PpG7 |
| naphthalene | ND[3] | 84.3 (± 2.3) | ND |
| 2-MN | ND | 85.7 (± 10.3) | ND |
| 1-MN | ND | 85.2 (± 7.3) | 64.5 (± 3.0) |
| biphenyl | ND | 86.6 (± 13.8) | 89.7 (± 1.8) |
| 2,6-DMN | ND | 91.4 (± 4.8) | 97.1 (± 2.9) |
| 2,3-DMN | ND | 78.9 (± 12.7) | 82.5 (± 2.5) |
| acenaphthene | ND | 96.3 (± 3.7) | 102.4 (± 0.8) |
| fluorene | ND | 106.2 (± 11.8) | 117.8 (± 10.7) |
| phenanthrene | ND | 91.2 (± 10.8) | 119.4 (± 11.4) |
| anthracene | 1.5 (± 1.5) | 91.5 (± 4.1) | 100.6 (± 1.6) |
| 2-MA | ND | 100.0 (± 30.0) | 67.0 (± 2.0) |
| anthraquinone | 6.5 (± 6.5) | 88.9 (± 17.8) | 85.6 (± 14.8) |
| fluoranthene | 69.5 (± 13.6) | 101.2 (± 9.8) | 102.1 (± 18.8) |
| pyrene | 44.3 (± 8.6) | 87.0 (± 8.7) | 108.9 (± 8.1) |
| 23-BBF | ND | 115.0 (± 15.0) | 120.0 (± 5.0) |
| chrysene | ND | 106.7 (± 16.3) | 126.7 (± 7.7) |
| benzo[a]pyrene | ND | 115.6 (± 7.7) | 114.0 (± 14.2) |

[1]See Table 1 for abbreviations used.
[2]fluoranthene-induced bacterial consortium killed with 5% formaldehyde (37% formalin solution) at the time of inoculation.
[3]ND = not detected (<0.01 mg/L).

With continued incubation, further degradation of the 4 compounds which were still present at 3 days was observed (Table 3). Following 5 days of incubation, anthracene and anthraquinone were no longer recoverable. The amount of fluoranthene extractable after 5, 8, and 14 days incubation decreased from 52.1 to 41.6 to 16.8%, respectively. Similarly, recovery of pyrene after 5, 8, and 14 days incubation decreased from 43.9 to 17.4 to 12.0%, respectively.

The relatively high recovery of fluoranthene from tubes inoculated with the fluoranthene-induced control requires clarification. Consortium biomass for inoculation was generated in MS+fluoranthene broth which contained an excess of insoluble fluoranthene (500 mg/L). It was later determined that there was a significant carry-over of fluoranthene from the cultures. It could be calculated that those tubes inoculated with the fluoranthene consortium received an additional 0.38 mg of fluoranthene (75.1 mg/L) resulting in an initial fluoranthene concentration of 83.8 mg/L. Therefore, after 3 days incubation, the fluorantheneinduced consortium had degraded 30% of the total amount of fluoranthene originally present or 0.13 mg fluoranthene.

TABLE 3

Continued loss of PAH's remaining after 3 days incubation.

| | % recovery of PAH's after extended incubation with the fluoranthene-induced consortium | | | |
|---|---|---|---|---|
| Compound | Day 3 | Day 5 | Day 8 | Day 14 |
| anthracene | 1.5 (± 1.5) | ND[1] | ND | ND |
| anthraquinone | 6.5 (± 6.5) | ND | ND | ND |
| fluoranthene | 69.5 (± 13.6) | 52.1 (± 22.3) | 41.6 (± 8.8) | 16.8 (± 6) |
| pyrene | 44.3 (± 8.6) | 43.9 (± 12.6) | 17.4 (± 7.0) | 12.0 (± 12) |

[1]ND = not detected (<0.01 mg/L).

The following Table 4 gives a partial characterization of the bacterial consortium:

TABLE 4

Partial characterization of the bacteria comprising the fluoranthene-utilizing community.

| Strain designation | Colony morphology[1] | Gram reaction |
|---|---|---|
| FAE1 | white, 1-2 mm mucoid | negative rods |
| FAE2 | light brown, 3-4 mm, mucoid | negative cocci |
| FAE3 | colorless, 1-2 mm, mucoid | negative cocci |
| FAE4 | white, 3-4 mm, slime producing | negative rods |
| FAE5 | bright yellow, 1-2 mm, mucoid | negative rods |
| FAE5b | opaque yellow, <1 mm, mucoid | negative rods |
| FAE6 | white, 4-5 mm, spreading | positive cocci |

[1]Colony morphology after 5 days incubation at 28° C. on NAG agar.

EXAMPLE 5

Preparation of Fluoranthene-Induced Cell Suspensions of Consortium

Fifty ml of MS+fluoranthene broth were transferred aseptically to a clean, sterile 250 ml Erlenmeyer flask fitted with Teflon-lined screw-caps, inoculated with the reconstituted bacterial consortium, and incubated (28° C., 175 cycles/min) for 10 days. After 10 days incubation, cultures were diluted 1:100 (vol/vol) in fresh MS+fluoranthene broth. Fluoranthene degradation was visually apparent after 2 days incubation at which time the consortium was diluted 1:25. Following 3 days incubation, fluoranthene-induced cells were concentrated (10,000 g, 10 min, 4° C.) and resuspended in 1/10 vol MS medium.

EXAMPLE 6

Action of Consortium Cells Towards PAH's

Suspensions of fluoranthene-induced cells of the consortium (100 µl) were used to inoculate 5.0 ml MS+PAH broth in clean, sterile 50.0 ml test tubes fitted with Teflon-lined screw-caps. Killed cell controls were generated by adding 250 µl of a 37% formalin solution to 8 of the 16 tubes inoculated with the fluoranthene-induced consortium. Uninoculated controls were also incorporated. In addition, 8 tubes containing MS+PAH broth were inoculated with 100 µl of cell suspension of Pseudomonas putida PpG7 (a gift from Dr. I. C. Gunsalus, University of Illiniois) which, in preliminary studies, demonstrated the ability to selectively utilize only 2 compounds (naphthalene and 2-methylnaphthalene) present in the defined PAH mixture. After 3, 5, 8, and 14 days incubation (28° C., 200 cycles/min), duplicate tubes of each treatment were removed and extracted from determination of PAH's present.

EXAMPLE 7

Methylene Chloride Extraction Procedure

At selected times, MS+PAH broth in a given tube was transferred to a clean, methylene chloride-rinsed, 15 ml glass conical extraction tube fitted with a Teflon-lined screw-cap. The original incubation tube was rinsed with 2.0 ml methylene chloride which was added to the extraction tube. Tubes were shaken for 1.0 min to facilitate the extraction of unmetabolized PAH's into the organic phase. Methylene chloride was separated from the aqueous phase after centrifugation (2500 g, 5 min). The entire separated organic phase (2.0 ml) was removed employing a methylene chloride-rinsed, 1.0 ml glass syringe fitted with a blunt-end needle, and transferred to a clean, solvent-rinsed concentration tube. The extraction procedure was repeated 2 more times with 0.5 ml methylene chloride. The final volume of methylene chloride (3.0 ml) was reduced to <1.0 ml under a stream of dry nitrogen. After the final volume of methylene chloride was adjusted to 1.0 ml, each extract was spiked with 10 μl of a 1,4-naphthaquinone solution (10 mg/ml methylene chloride) as a marker and transferred to a GC vial for subsequent analysis.

EXAMPLE 8

Capillary Gas Chromatography

Gas chromatographic analysis of methylene chloride extracts and of individual PAH standards was performed on a Hewlett-Packard model 5710A gas chromatographic equipped with a flame ionization detector. Hydrogen was used as carrier gas (0.5 ml/min) while air (240 ml/min) and hydrogen (30 ml/min) was supplied for the flame ionization detector. Polycyclic aromatic hydrocarbons in replicate 1.0 μl injections were separated on a 15.0 m×0.32 mm I.D. SPB-5 (Supelco, Bellefonte, Pa.) capillary column with a 0.25 μm coating phase. Oven temperature was programmed at 80° C. for 2 min followed by a linear increase of 8° C./min to 280° C. where it was held for 4 min (30 min run). Injector and detector temperatures were maintained at 270° C. Percent recovery of each PAH was calculated by comparing peak area with that of standards for each compound.

We claim:

1. A biologically pure culture of *Pseudomonas paucimobilis* strain EPA505sc., having all of the identifying characteristics of deposit NRRL B-18512.

UNITED STATES PATENT AND TRADEMARK OFFICE
CERTIFICATE OF CORRECTION

PATENT NO.  :  5,242,825

DATED       :  September 7, 1993

INVENTOR(S) :  James G. Mueller, Peter J. Chapman

It is certified that error appears in the above-identified patent and that said Letters Patent is hereby corrected as shown below:

Column 2:  line 36:  "associated wtih" should read --associated with--.
Column 7:  line 61:  "colonies is each" should read --colonies of each--.
Column 9:  line 51:  "fluorantheneinduced" should read --fluoranthene-induced--.

Signed and Sealed this

Twenty-sixth Day of April, 1994

Attest:

BRUCE LEHMAN

Attesting Officer　　　　Commissioner of Patents and Trademarks